(12) United States Patent
Farritor et al.

(10) Patent No.: US 8,894,633 B2
(45) Date of Patent: *Nov. 25, 2014

(54) MODULAR AND COOPERATIVE MEDICAL DEVICES AND RELATED SYSTEMS AND METHODS

(75) Inventors: Shane M. Farritor, Lincoln, NE (US); Mark Rentschler, Boulder, CO (US); Amy Lehman, York, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 403 days.

This patent is subject to a terminal disclaimer.

(21) Appl. No.: 12/971,917

(22) Filed: Dec. 17, 2010

(65) Prior Publication Data

US 2011/0237890 A1   Sep. 29, 2011

Related U.S. Application Data

(60) Provisional application No. 61/287,628, filed on Dec. 17, 2009.

(51) Int. Cl.
*A61B 17/00* (2006.01)

(52) U.S. Cl.
USPC .................................................. 606/1

(58) Field of Classification Search
CPC ....................................................... A61B 19/22
USPC .................................................. 606/1
See application file for complete search history.

(56) References Cited

U.S. PATENT DOCUMENTS

| | | |
|---|---|---|
| 3,870,264 A | 3/1975 | Robinson |
| 3,989,952 A | 11/1976 | Hohmann |
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |

(Continued)

FOREIGN PATENT DOCUMENTS

| | | |
|---|---|---|
| EP | 2286756 A1 | 2/2011 |
| JP | 2004144533 | 5/1990 |

(Continued)

OTHER PUBLICATIONS

Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.

(Continued)

*Primary Examiner* — Gary Jackson
*Assistant Examiner* — John R Downey
(74) *Attorney, Agent, or Firm* — Davis, Brown, Koehn, Shors & Roberts, P.C.; Sean D. Solberg

(57) ABSTRACT

The various embodiments disclosed herein relate to modular medical devices, including various devices with detachable modular components and various devices with pivotally attached modular components. Additional embodiments relate to procedures in which various of the devices are used cooperatively. Certain embodiments of the medical devices are robotic in vivo devices.

16 Claims, 10 Drawing Sheets

(56) References Cited

U.S. PATENT DOCUMENTS

| | | |
|---|---|---|
| 4,897,014 A | 1/1990 | Tietze |
| 4,922,755 A | 5/1990 | Oshiro et al. |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,674,030 A | 10/1997 | Sigel |
| 5,728,599 A | 3/1998 | Rostoker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,900 A | 8/1998 | Madhani et al. |
| 5,807,377 A | 9/1998 | Madhani et al. |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,911,036 A | 6/1999 | Wright et al. |
| 5,971,976 A | 10/1999 | Wang et al. |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Okamoto et al. |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Tierney et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |

(56) References Cited

U.S. PATENT DOCUMENTS

| | | |
|---|---|---|
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,179,073 B2 | 5/2012 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0026186 A1 | 2/2002 | Woloszko et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |

(56) References Cited

U.S. PATENT DOCUMENTS

| | | |
|---|---|---|
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0106916 A1 | 6/2004 | Quaid et al. |
| 2004/0111113 A1 | 6/2004 | Nakamura et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0164079 A1 | 7/2008 | Jacobsen |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2009/0020724 A1 | 1/2009 | Paffrath |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0143787 A9 | 6/2009 | De La Pena |
| 2009/0171373 A1 | 7/2009 | Farritor et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0081875 A1 | 4/2010 | Fowler et al. |
| 2010/0198231 A1 | 8/2010 | Scott |
| 2010/0204713 A1 | 8/2010 | Ruiz |
| 2010/0245549 A1 | 9/2010 | Allen et al. |
| 2010/0318059 A1 | 12/2010 | Farritor et al. |
| 2011/0015569 A1 | 1/2011 | Kirschenman et al. |
| 2011/0077478 A1 | 3/2011 | Freeman et al. |
| 2011/0152615 A1 | 6/2011 | Schostek et al. |
| 2011/0224605 A1 | 9/2011 | Farritor et al. |
| 2011/0237890 A1 | 9/2011 | Farritor et al. |
| 2012/0035582 A1 | 2/2012 | Nelson et al. |
| 2013/0041360 A1 | 2/2013 | Farritor |

FOREIGN PATENT DOCUMENTS

| | | |
|---|---|---|
| JP | 5115425 | 5/1993 |
| JP | 6-508049 | 9/1994 |
| JP | 07 136173 | 5/1995 |
| JP | 7306155 | 11/1995 |
| JP | 2004322310 | 6/2004 |
| JP | 2004180781 | 7/2004 |
| JP | 2004329292 | 11/2004 |
| WO | WO 92/21291 | 5/1991 |
| WO | WO 02/082979 | 10/2002 |
| WO | WO 02/100256 | 12/2002 |
| WO | WO 2005/009211 | 2/2005 |
| WO | WO 2006 005075 | 1/2006 |
| WO | WO 2006/079108 | 1/2006 |
| WO | WO 2006/052927 | 5/2006 |
| WO | WO 2007/111571 | 10/2007 |
| WO | WO 2007/149559 | 12/2007 |
| WO | WO 2009/144729 | 12/2009 |
| WO | WO 2010/042611 | 4/2010 |
| WO | WO2010/042611 | 4/2010 |
| WO | WO 2010/046823 | 4/2010 |
| WO | WO2010/046823 | 4/2010 |
| WO | WO 2011/135503 A1 | 11/2011 |

OTHER PUBLICATIONS

Abbou et al., "Laparoscopic Radical Prostatectomy with a Remote Controlled Robot," The Journal of Urology, Jun. 2001, 165: 1964-1966.

Allendorf et al., "Postoperative Immune Function Varies Inversely with the Degree of Surgical Trauma in a Murine Model," Surgical Endoscopy 1997; 11: 427-430.

Ang, "Active Tremor Compensation in Handheld Instrument for Microsurgery," Doctoral dissertation, tech report CMU-RI-TR-04-

(56) References Cited

OTHER PUBLICATIONS

28, Robotics Institute, Carnegie Mellon University, May 2004, 167 pp.
Applicant Amendment after Notice of Allowance under Rule 312, filed Aug. 25, 2008, in related case U.S. Appl. No. 11/695,944, 6 pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8 pp.
Applicant Response to Office Action dated Aug. 21, 2006, in related case U.S. Appl. No. 11/403,756, filed Nov. 21, 2006, 52 pp.
Applicant Response to Office Action dated Oct. 29, 2007, in related case U.S. Appl. No. 11/695,944, filed Jan. 22, 2008, 6 pp.
Atmel 80C5X2 Core, http://www.atmel.com, 2006, 186 pp.
Bailey et al., "Complications of Laparoscopic Surgery," Quality Medical Publishers, Inc., 1995, 25 pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; I9(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., "Multiple Arterial Conduits Without Cardiopulmonary Bypass: Early Angiographic Results," Ann Thorac Surg, 1999; 67: 450-456.
Camarillo et al., "Robotic Technology in Surgery: Past, Present, and Future," The American Journal of Surgery, 2004; 188: 2S-15.
Cavusoglu et al., "Telesurgery and Surgical Simulation: Haptic Interfaces to Real and Virtual Surgical Environments," In McLaughlin, M. L., Hespanha, J. P., and Sukhatme, G., editors. Touch in virtual environments, IMSC Series in Multimedia 2001, 28 pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al. (2003), "Measuring Forces in Liver Cutting: New Equipment and Experimental Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4 pp.
CrystalEyes, http://www.reald.com, 2007 (Stere03D visualization for CAVEs, theaters and immersive environments), I pg.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving In Vivo Robot Vision Quality," from the Proceedings of Medicine Meets Virtual Reality, Long Beach, CA, Jan. 26-29, 2005, 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2 pp.
Falcone et al., "Robotic Surgery," Clin. Obstet. Gynecol. 2003, 46(1): 37-43.
Faraz et al., "Engineering Approaches to Mechanical and Robotic Design for Minimally Invasive Surgery (MIS)," Kluwer Academic Publishers (Boston), 2000, 13 pp.
Fearing et al., "Wing Transmission for a Micromechanical Flying Insect," Proceedings of the 2000 IEEE International Conference on Robotics & Automation, Apr. 2000; 1509-1516.
Fireman et al., "Diagnosing small bowel Crohn's disease with wireless capsule endoscopy," Gut 2003; 52: 390-392.
Flynn et al, "Tomorrow's surgery: micromotors and microrobots for minimally invasive procedures," Minimally Invasive Surgery & Allied Technologies, 1998; 7(4): 343-352.
Franklin et al., "Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6): 1317-1320.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committee," U.S. Food and Drug Administration, available at http://www.fdaJ:?;ov, Finalized: Nov. 7, 2003; Updated: Jun. 24, 2005, 11 pp.
Glukhovsky et al., "The development and application of wireless capsule endoscopy," Int. J. Med. Robot. Comput. Assist. Surgery, 2004; I (1): 114-123.
Gong et al., Wireless endoscopy, Gastrointestinal Endoscopy 2000; 51(6): 725-729.
Grady, "Doctors Try New Surgery for Gallbladder Removal," The New York Times, Apr. 20, 2007, 3 pp.
Guber et al., "Miniaturized Instrument Systems for Minimally Invasive Diagnosis and Therapy," Biomedizinische Technic. 2002, Band 47, Erganmngsband 1: 198-201.
Guo et al., "Fish-like Underwater Microrobot with 3 DOF," Proceedings of the 2002 IEEE International Conference on Robotics & Automation, May 2002: 738-743.
Guo et al., "Micro Active Guide Wire Catheter System—Characteristic Evaluation, Electrical Model and Operability Evaluation of Micro Active Catheter," Proceedings of the 1996 IEEE International Conference on Robotics and Automation, Apr. 1996: 2226-2231.
Hanly et al., "Robotic Abdominal Surgery," The American Journal of Surgery 188 (Suppl.to Oct. 1994): 19S-26S, 2004.
Hanly et al., "Value of the SAGES Learning Center in introducing new technology," Surgical Endoscopy, 2004; 19(4): 477-483.
Heikkinen et al., "Comparison of laparoscopic and open Nissen fundoplication two years after operation: A prospective randomized trial," Surgical Endoscopy, 2000; 14: 1019-1023.
Hissink, "Olympus Medical develops capsule camera technology," Dec. 2004, accessed Aug. 29, 2007, http://www.letsgodigital.org , 3 pp.
Horgan et al., "Technical Report: Robots in Laparoscopic Surgery," Journal of Laparoendoscopic & Advanced Surgical Techniques, 2001; 11(6): 415-419.
International Preliminary Report on Patentability from related case PCT/US2007/014567, mailed Jan. 8, 2009, 11 pp.
International Search Report and Written Opinion from international application No. PCT/US07/14567, mailed Apr. 28, 2008, 19 pp.
International Search Report and Written Opinion from international application No. PCT/US2007/089191, mailed Nov. 10, 2008, 20 pp.
International Search Report and Written Opinion of international application No. PCT/US2008/073369, mailed Nov. 12, 2008, 12 pp.

(56) References Cited

OTHER PUBLICATIONS

International Search Report and Written Opinion of international application No. PCT/US2008/073334, mailed Jan. 12, 2009, 11 pp.
International Search Report and Written Opinion of international application No. PCT/US2008/069822, mailed Aug. 5, 2009, 12 pp.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005; 15: 2045-2055.
Meron, "The development of the swallowable video capsule (M2A)," Gastrointestinal Endoscopy 2000; 52 6: 817-819.
Micron, http://www.micron.com, 2006, I/4-inch VGA NTSC/PAL CMOS Digital Image Sensor, 98 pp.

Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on Computational Intelligence, Robotics and Autonomous Systems (CIRAS 2001), Nov. 28-30, 2001, Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.
Preliminary Amendment filed Apr. 11, 2007, in related case U.S. Appl. No. 11/403,756, 7 pp.
Preliminary Amendment filed Jul. 30, 2008, in related case U.S. Appl. No. 12/171,413, 4 pp.
RCE and Amendment filed Jun. 13, 2007, in related case U.S. Appl. No. 11/403,756, 8 pp.
Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.

(56) References Cited

OTHER PUBLICATIONS

Rentschler et al., Mobile In Vivo Biopsy Robot, IEEE International Conference on Robotics and Automation, Orlando, Florida, May 2006, pp. 4155-4160.
Rentschler et al., "Miniature in vivo Robots for Remote and Harsh Environments," IEEE Transactions on Information Technology in Biomedicine, Jan. 2006; 12(1): 66-75.
Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, I pg.
Rentschler et al., "In Vivo Robots for Laparoscopic Surgery," Studies in Health Technology and Informatics—Medicine Meets Virtual Reality, ISO Press, Newport Beach, CA, 2004a, 98: 316-322.
Rentschler et al., "Mechanical Design of Robotic In Vivo Wheeled Mobility," ASME Journal of Mechanical Design, 2006a, pp, I-II.
Rentschler et al., "Mobile In Vivo Camera Robots Provide Sole Visual Feedback for Abdominal Exploration and Cholecystectomy," Journal of Surgical Endoscopy, 20-I: 135-138, 2006b.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Informatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Informatics-Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Informatics-Medicine Meets Virtual Reality, pp. 442-448, Jan. 2005.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al, "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fastastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al. (1993), "Sensing and Manipulation Problems in Endoscopic Surgery: Experiment, Analysis, and Observation," Presence 2( 1): 66-81.
Tendick et al., "Applications of Micromechatronics in Minimally Invasive Sugery, " IEEE/ASME Transaction on Mechatronicsm 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
Way et al (editors), "Fundamentals of Laparoscopic Surgery," Churchill Livingstone Inc., 1995, 14 pp.
Wolfe et al, "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imaging," vol. 25, No. 1, Gastroenterology Nursing, pp. 24-27.
Abbott et al., "Design of an Endoluminal NOTES Robotic System," from the Proceedings of the 2007 IEEE/RSJ Intl Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.

(56) References Cited

OTHER PUBLICATIONS

Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 80C5X2 Core, http://www.atmel.com, 2006, 186pp.
Bailey et al., "Complications of Laparoscopic Surgery," Quality Medical Publishers, Inc., 1995, 25pp.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al, "Telesurgery and Surgical Simulation: Haptic Interlaces to Real and Virtual Surgical Environments," In McLaughliin, M.L., Hespanha, J.P., and Sukhatme, G., editors. Touch in virtual environments, IMSC Series in Multimedia 2001, 28pp.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Dumpert et al., "Improving in Vivo Robot Visioin Quality," from the Proceedings of Medicine Meets Virtual Realtiy, Long Beach, CA, Jan. 26-29, 2005. 1 pg.
Examiner Interview Summary dated Nov. 30, 2006, in related case U.S. Appl. No. 11/398,174, 2pp.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Flynn et al., "Tomorrow's Surgery: micromotors and microbots for minimally invasive procedures," Minimally Invasive Surgery & Allied Technologies.
Franzino, "The Laprotek Surgical System and the Next Generation of Robotics," Surg Clin North Am, 2003 83(6):.
Fraulob et al., "Miniature assistance module for robot-assisted heart surgery," Biomed. Tech. 2002, 47 Suppl. 1, Pt. 1:12-15.
Fukuda et al., "Micro Active Catheter System with Multi Degrees of Freedom," Proceedings of the IEEE International Conference on Robotics and Automation, May, 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Guber et al., "Miniaturized Instrumetn Systems for Minimally Invasive Diagnosis and Therapy," Biomedizinishe Technic. 2002, Band 47, Erganmngsband 1.
Tendick et al., "Applications of Micromechatronics in Minimally Invasive Surgery," IEEE/ASME Transactions on Mechatronics, 1998; 3(1): 34-42.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Yu, BSN, RN, "M2ATM Capsule Endoscopy a Breakthrough Diagnostic Tool for Small Intestine Imagining," vol. 25, No. 1, Gastroenterology Nursing, pp. 24-27.
International Search Report and Written Opinion of international application No. PCT/US2010/061137, mailed Feb. 11, 2011, 10 pp.
Glukhovsky et al.., "The development and application of wireless capsule endoscopy," Int. J. Med. Robot. Comput. Assist. Surgery, 2004; I (1): 114-123.
Gong et al., "Wireless endoscopy," Gastrointestinal Endoscopy 2000; 51(6): 725-729.
Hanly et al., "Value of the SAGES Learning Center in introducing new technology," Surgical Endoscopy, 2004; 19 (4): 477-483.
Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e
Rentschler et al., "Mobile In Vivo Biopsy Robot," IEEE International Conference on Robotics and Automation, Orlando, Florida, May 2006, pp. 4155-4160.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Informatics—Medicine Meets Virtual Reality, Jan. 2001, 7 pp.
Rosen et al., "Spherical Mechanism Analysis of a Surgical Robot for Minimally Invasive Surgery—Analytical and Experimental Approaches," Studies in Health Technology and Informatics—Medicine Meets Virtual Reality, pp. 442-448, Jan. 2005.
Ruurda et al., "Robot-Assisted surgical systems: a new era in laparoscopic surgery," Ann R. Coll Surg Engl., 2002; 84: 223-226.
Slatkin et al., "The Development of a Robotic Endoscope," Proceedings of the 1995 IEEE International Conference on Robotics and Automation, pp. 162-71, 1995.
Smart Pill "Fantastic Voyage: Smart Pill to Expand Testing," http://www.smartpilldiagnostics.com, Apr. 13, 2005, 1 pg.
Stiff et al.., "Long-term Pain: Less Common After Laparoscopic than Open Cholecystectomy," British Journal of Surgery, 1994; 81: 1368-1370.
Tendick et al.. (1993), "Sensing and Manipulation Problems in Endoscopic Surgery: Experiment, Analysis, and Observation," Presence 2( 1): 66-81.
International Search report and Written Opinion from international application No. PCT/US2012/41911, mailed Mar. 13, 2013.
International Search Report and Written Opinion from international application No. PCT/US12/46274, mailed Sep. 25, 2012.
"International Search Report and Written Opinion from international application No. PCT/US07/14567, mailed Apr. 28, 2008, 19 pp."
International Search Report and Written Opinion issued in PCT/US11/46809, mailed Dec. 8, 2011.
Micron, http://www.micron.com, 2006, 1/4-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.

(56) References Cited

OTHER PUBLICATIONS

International Search Report and Written Opinion issued in PCT/US2010/061137, mailed Feb. 11, 2011, 10 pages.

Midday, Jeff et al., "Material Handling System for Robotic natural Orifice Surgery", Proceedings of the 2011 Design of medical Devices Conference, Apr. 12-14, 2011, Minneapolis, MN, 4 pages.

Palm, William, "Rapid Prototyping Primer" May 1998 (revised Jul. 30, 2002) (http://www.me.psu.edu/lamancusa/rapidpro/primer/chapter2.htm).

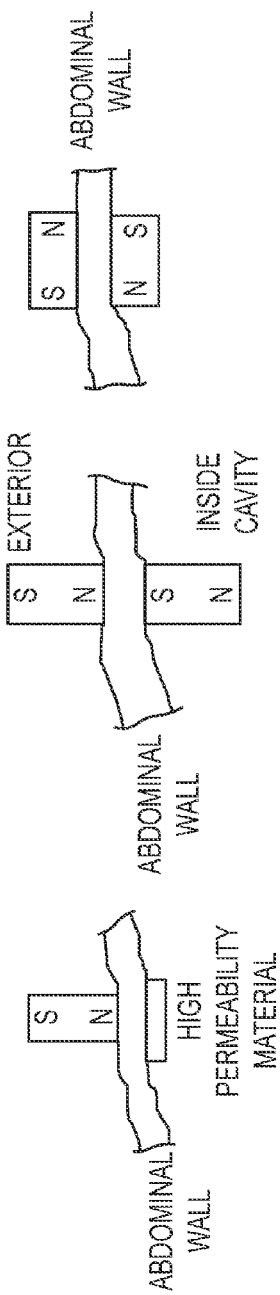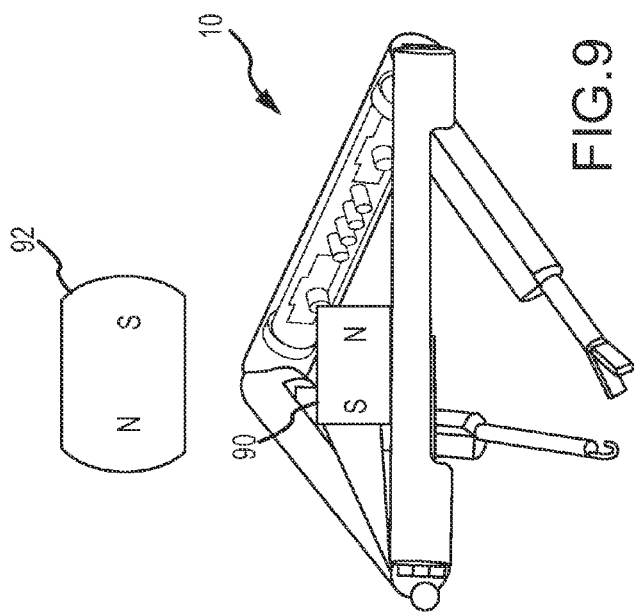

UNSTABLE

STABLE

MODULAR AND COOPERATIVE MEDICAL DEVICES AND RELATED SYSTEMS AND METHODS

CROSS-REFERENCE TO RELATED APPLICATIONS

This application claims priority to Provisional Application No. 61/287,628, filed on Dec. 17, 2010, which is hereby incorporated herein by reference in it's entirety.

GOVERNMENT SUPPORT

This invention was made with government support under Grant No. R21EB5663-2, awarded by the National Institute of Biomedical Imaging and Bioengineering within the National Institutes of Health. Accordingly, the government has certain rights in the invention.

TECHNICAL FIELD

The embodiments disclosed herein relate to various medical devices and related components, including robotic and/or in vivo medical devices and related components. Certain embodiments include various modular medical devices, including modular in vivo and/or robotic devices. Other embodiments relate to modular medical devices in which the various modular components are segmented components or components that are coupled to each other. Further embodiment relate to methods of operating the above devices, including methods of using various of the devices cooperatively.

BACKGROUND

Invasive surgical procedures are essential for addressing various medical conditions. When possible, minimally invasive procedures such as laparoscopy are preferred.

However, known minimally invasive technologies such as laparoscopy are limited in scope and complexity due in part to 1) mobility restrictions resulting from using rigid tools inserted through access ports, and 2) limited visual feedback. Known robotic systems such as the da Vinci® Surgical System (available from Intuitive Surgical, Inc., located in Sunnyvale, Calif.) are also restricted by the access ports, as well as having the additional disadvantages of being very large, very expensive, unavailable in most hospitals, and having limited sensory and mobility capabilities.

There is a need in the art for improved surgical methods, systems, and devices.

BRIEF DESCRIPTION OF THE DRAWINGS

FIGS. 8A-8C are schematic representations of various magnetic attachment mechanisms, according to various embodiments.
FIG. 9 is a perspective view of the device of FIG. 1A.

DETAILED DESCRIPTION

Figure 1A:
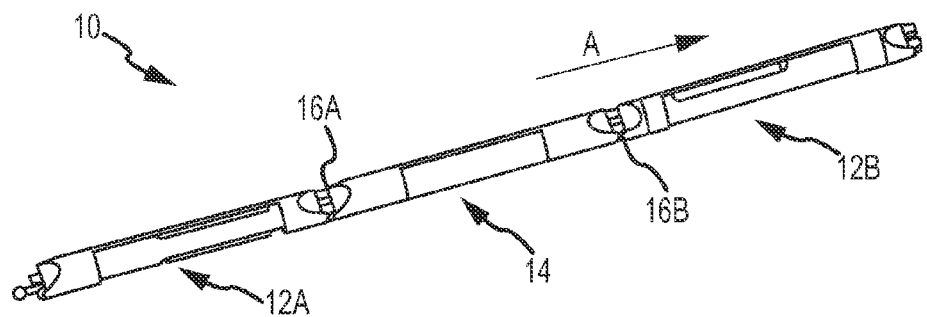
FIG. 1A is a perspective view of a modular medical device, according to another embodiment.

The various systems and devices disclosed herein relate to devices for use in medical procedures and systems. More specifically, various embodiments relate to various modular or combination medical devices, including modular in vivo and robotic devices and related methods and systems, while other embodiments relate to various cooperative medical devices, including cooperative in vivo and robotic devices and related methods and systems.

It is understood that the various embodiments of modular and cooperative devices and related methods and systems disclosed herein can be incorporated into or used with any other known medical devices, systems, and methods.

For example, the various embodiments disclosed herein may be incorporated into or used with any of the medical devices and systems disclosed in copending U.S. application Ser. No. 12/192,779 (filed on Aug. 15, 2008 and entitled "Modular and Cooperative Medical Devices and Related Systems and Methods"), Ser. No. 11/932,441 (filed on Oct. 31, 2007 and entitled "Robot for Surgical Applications"), Ser. No. 11/695,944 (filed on Apr. 3, 2007 and entitled "Robot for Surgical Applications"), Ser. No. 11/947,097 (filed on Nov. 27, 2007 and entitled "Robotic Devices with Agent Delivery Components and Related Methods), Ser. No. 11/932,516 (filed on Oct. 31, 2007 and entitled "Robot for Surgical Applications"), Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), Ser. No. 12/171,413 (filed on Jul. 11, 2008 and entitled "Methods and Systems of Actuation in Robotic Devices"), 60/956,032 (filed on Aug. 15, 2007), 60/983,445 (filed on Oct. 29, 2007), 60/990,062 (filed on Nov. 26, 2007), 60/990,076 (filed on Nov. 26, 2007), 60/990,086 (filed on Nov. 26, 2007), 60/990,106 (filed on Nov. 26, 2007), 60/990,470 (filed on Nov. 27, 2007), 61/025,346 (filed on Feb. 1, 2008), 61/030, 588 (filed on Feb. 22, 2008), and 61/030,617 (filed on Feb. 22, 2008), all of which are hereby incorporated herein by reference in their entireties.

Certain device implementations disclosed in the applications listed above can be positioned within a body cavity of a patient, including certain devices that can be positioned against or substantially adjacent to an interior cavity wall, and related systems. An "in vivo device" as used herein means any device that can be positioned, operated, or controlled at least in part by a user while being positioned within a body cavity of a patient, including any device that is positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Certain implementations disclosed herein relate to "combination" or "modular" medical devices that can be assembled in a variety of configurations. For purposes of this application, both "combination device" and "modular device" shall mean any medical device having modular or interchangeable components that can be arranged in a variety of different configurations. The modular components and combination devices disclosed herein also include segmented triangular or quadrangular-shaped combination devices. These devices, which are made up of modular components (also referred to herein as "segments") that are connected to create the triangular or quadrangular configuration, can provide leverage and/or stability during use while also providing for substantial payload space within the device that can be used for larger components or more operational components. As with the various combination devices disclosed and discussed above, according to one embodiment these triangular or quadrangular devices can be positioned inside the body cavity of a patient in the same fashion as those devices discussed and disclosed above.

FIGS. 1A-7 depict a multi-segmented medical device 10, in accordance with one implementation. According to one embodiment, the device 10 is a robotic device 10 and further can be an in vivo device 10. This device embodiment 10 as shown includes three segments 12A, 12B, 14. Segments 12A and 12B are manipulator segments, while segment 14 is a command and imaging segment. Alternatively, the three segments can be any combination of segments with any combination of components and capabilities. For example, according to an alternative embodiment, the device could have one manipulator segment, one command and imaging segment, and a sensor segment. In a further alternative, the various segments can be any type of module, including any of those modules described above with respect to other modular components discussed herein.

Figure 1B:
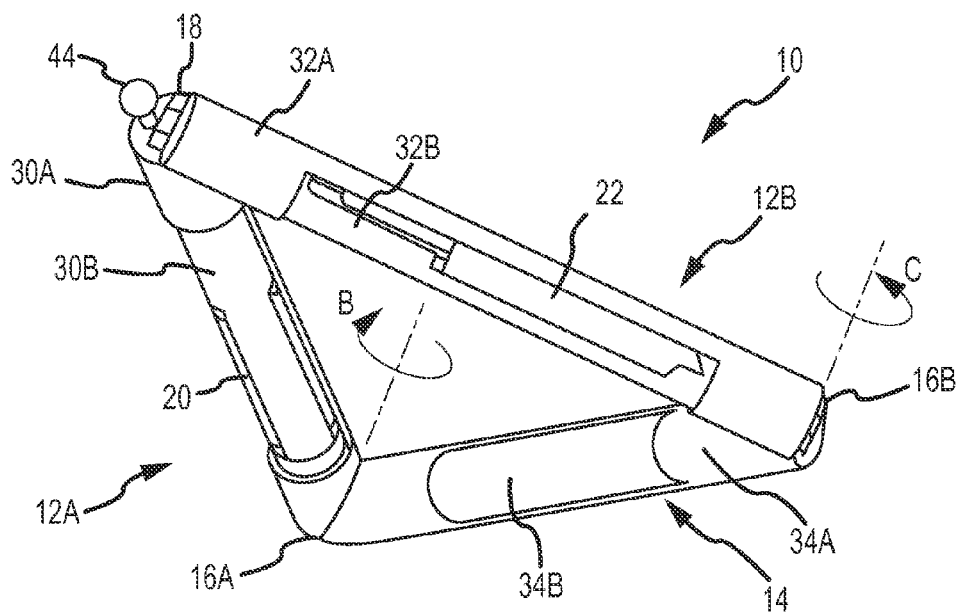
FIG. 1B is a perspective bottom view of the device of FIG. 1A.

As best shown in FIGS. 1A and 1B, segments 12A, 12B are rotatably coupled with the segment 14 via joints or hinges 16A, 16B. More specifically, segment 12A is rotatable relative to segment 14 about joint 16A around an axis as indicated by arrow B in FIG. 1B, while segment 12B is rotatable relative to segment 14 about joint 16B around an axis as indicated by arrow C in FIG. 1B.

In accordance with one embodiment, the device 10 has at least two configurations. One configuration is an extended or insertion configuration as shown in FIG. 1A in which the three segments 12A, 12B, 14 are aligned along the same axis. The other configuration is a triangle configuration as shown in FIG. 1B in which the manipulator segments 12A, 12B are each coupled to the segment 14 via the joints 16A, 16B and further are coupled to each other at a coupleable connection 18 at the ends of the segments 12A, 12B opposite the joints 16A, 16B.

Figure 2A:
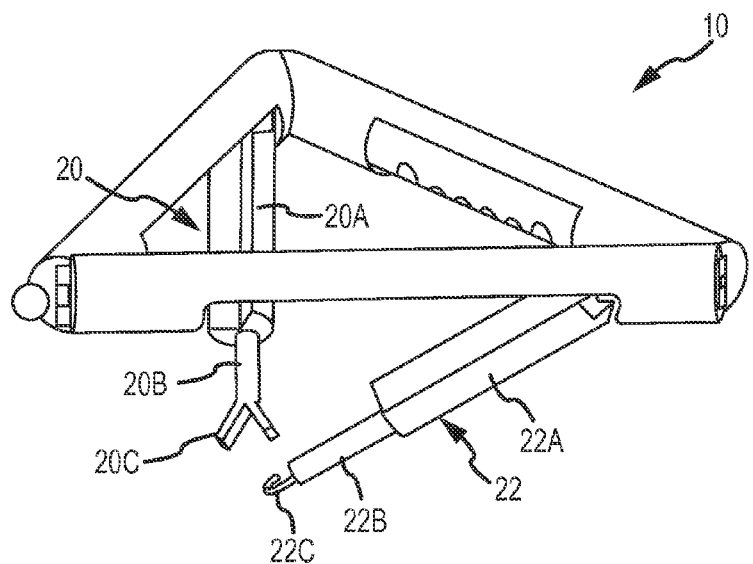
FIG. 2A is a perspective top view of the device of FIG. 1A.
Figure 3:
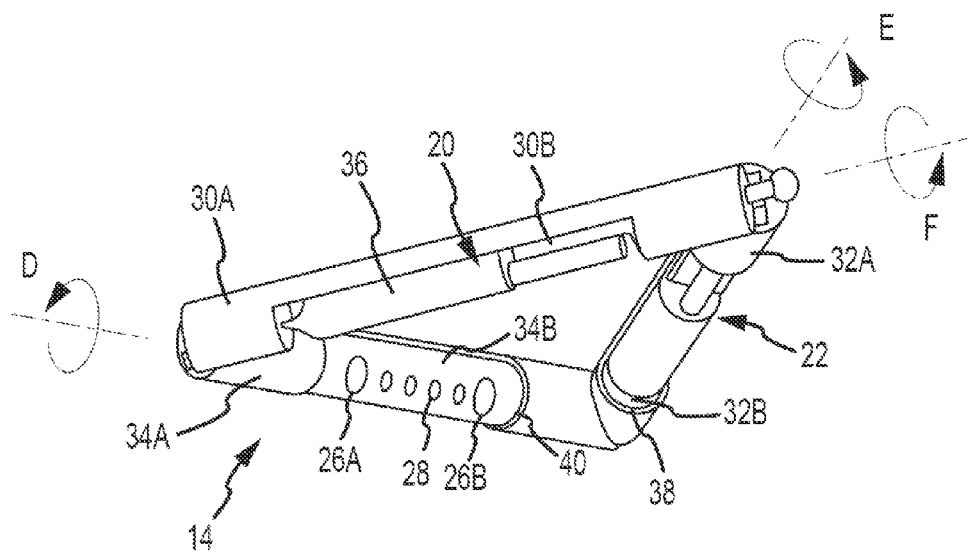
FIG. 3 is a perspective bottom view of the device of FIG. 1A.
Figure 4:
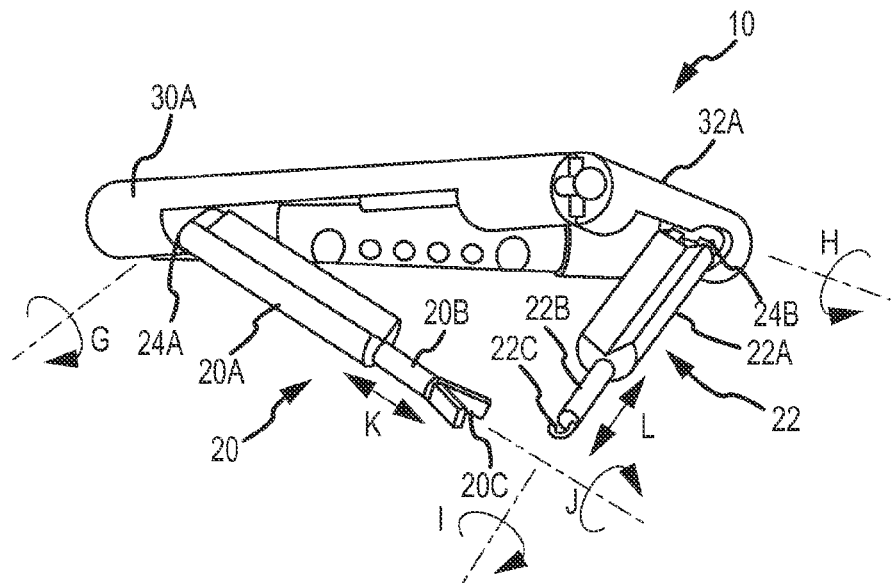
FIG. 4 is a perspective side view of the device of FIG. 1A.

As best shown in FIG. 2A, each of the manipulator segments 12A, 12B in this particular embodiment has an operational arm 20, 22 (respectively). Each arm 20, 22 is moveably coupled to its respective segment 12A, 12B at a joint 24A, 24B (respectively) (as best shown in FIG. 4). Further, segment 14 has a pair of imaging components (each also referred to herein as a "camera") 26A, 26B (as best shown in FIG. 3).

In one embodiment, each arm 20, 22 is configured to rotate at its joint 24A, 24B in relation to its segment 12A, 12B to move between an undeployed position in which it is disposed within its segment 12A, 12B as shown in FIG. 1B and a deployed position as shown in FIG. 2A. In one example, arm 20 is rotatable relative to segment 12A about joint 24A in the direction shown by G in FIG. 4, while arm 22 is rotatable relative to segment 12B about joint 24B in the direction shown by H in FIG. 4. Alternatively, the arms 20, 22 are moveable in relation to the segments 12A, 12B in any known fashion and by any known mechanism.

According to one embodiment as best shown in FIG. 2A, each arm 20, 22 has three components: a proximal portion 20A, 22A, a distal portion 20B, 22B, and an operational component 20C, 22C coupled with the distal portion 20B, 22B, respectively. In this embodiment, the distal portion 20B, 22B of each arm 20, 22 extends and retracts along the arm axis in relation to the proximal portion 20A, 22A while also rotating around that axis in relation to the proximal portion 20A, 22A. That is, distal portion 20B of arm 20 can move back and forth laterally as shown by the letter K in FIG. 4 and further can rotate relative to the proximal portion 20A as indicated by the letter J, while distal portion 22B of arm 22 can move back and forth laterally as shown by the letter L in FIG. 4 and further can rotate relative to the proximal portion 22A as indicated by the letter I.

In accordance with one implementation, the operational components 20C, 22C (also referred to herein as "end effectors") depicted in FIG. 2A are a grasper 20C and a cautery hook 22C. It is understood that the operational component(s) used with the device 10 or any embodiment herein can be any known operational component for use with a medical device, including any of the operational components discussed above with other medical device embodiments and further including any operational components described in the applications incorporated above. Alternatively, only one of the two arms 20, 22 has an operational component. In a further alternative, neither arm has an operational component.

Alternatively, each arm 20, 22 comprises one unitary component or more than two components. It is further understood that the arms 20, 22 can be any kind of pivotal or moveable arm for use with a medical device which may or may not have operational components coupled or otherwise associated with them. For example, the arms 20, 22 can have a structure or configuration similar to those additional arm embodiments discussed elsewhere herein or in any of the applications incorporated above. In a further alternative, the device 10 has only one arm. In a further alternative, the device 10 has no arms. In such alternative implementations, the segment(s) not having an arm can have other components associated with or coupled with the segment(s) such as sensors or other types of components that do not require an arm for operation.

As discussed above, the segment 14 of the embodiment depicted in FIG. 3 has a pair of cameras 26A, 26B. Alternatively, the segment 14 can have a single camera or more than two cameras. It is understood that any known imaging component for medical devices, including in vivo devices, can be used with the devices disclosed herein and further can be positioned anywhere on any of the segments or on the arms of the devices.

In a further embodiment, the segment 14 as best shown in FIG. 3 can also include a lighting component 28. In fact, the segment 14 has four lighting components 28. Alternatively, the segment 14 can have any number of lighting components 28 or no lighting components. In a further alternative, the device 10 can have one or more lighting components positioned elsewhere on the device, such as one or both of segments 12A, 12B or one or more of the arms, etc.

In accordance with a further embodiment as best shown in FIGS. 1B and 3, each of the segments 12A, 12B, 14 has two cylindrical components—an outer cylindrical component and an inner cylindrical component—that are rotatable in relation to each other. More specifically, the segment 12A has an outer cylindrical component 30A and an inner cylindrical component 30B that rotates relative to the outer component 30A around an axis indicated by arrow F in FIG. 3. Similarly, the segment 12B has an outer cylindrical component 32A and an inner cylindrical component 32B that rotates relative to the outer component 32A around an axis indicated by arrow E in FIG. 3. Further, the segment 14 has an outer cylindrical component 34A and an inner cylindrical component 34B that rotates relative to the outer component 34A around an axis indicated by arrow D in FIG. 3.

In use, the embodiments having rotatable cylindrical components as described in the previous paragraph can provide for enclosing any arms, cameras, or any other operational components within any of the segments. Further, any segment having such rotatable components provide for two segment configurations: an open configuration and a closed configuration. More specifically, segment 12A has an outer cylindrical component 30A with an opening 36 as shown in FIG. 3 through which the arm 20 can move between its deployed and undeployed positions. Similarly, segment 12B has an outer cylindrical component 32A with an opening 38 as shown in FIG. 3 through which the arm 22 can move between its deployed and undeployed positions. Further, segment 14 has an outer cylindrical component 34A with an opening 40 as shown in FIG. 3 through which the imaging component(s) 26A, 26B can capture images of a procedural or target area adjacent to or near the device 10.

FIG. 1B depicts the segments 12A, 12B, 14 in their closed configurations. That is, each of the inner cylindrical components 30B, 32B, 34B are positioned in relation to the respective outer cylindrical component 30A, 32A, 34A such that each opening 36, 38, 40, respectively, is at least partially closed by the inner component 30B, 32B, 34B such that the interior of each segment 12A, 12B, 14 is at least partially inaccessible from outside the segment.

More specifically, in the closed position, inner cylindrical component 30B of segment 12A is positioned in relation to outer cylindrical component 30A such that the arm 20 is at least partially enclosed within the segment 12A. According to one embodiment, the inner cylindrical component 30B is configured such that when it is in the closed position as shown in FIG. 1B, it closes off the opening 36 entirely. In a further embodiment, the inner cylindrical component 30B in the closed position fluidically seals the interior of the segment 12A from the exterior.

Similarly, in the closed position, inner cylindrical component 32B of segment 12B is positioned in relation to the outer cylindrical component 32A such that the arm 22 is at least partially enclosed within the segment 12B. According to one embodiment, the inner cylindrical component 32B is configured such that when it is in the closed position as shown in FIG. 1B, it closes off the opening 38 entirely. In a further embodiment, the inner cylindrical component 32B in the closed position fluidically seals the interior of the segment 12B from the exterior.

Further, in the closed position, inner cylindrical component 34B of segment 14 is positioned in relation to the outer cylindrical component 34A such that the imaging component(s) is not positioned within the opening 40. According to one embodiment, the inner cylindrical component 34B is configured such that when it is in the closed position as shown in FIG. 1B, the imaging component(s) and any lighting component(s) are completely hidden from view and not exposed to the exterior of the segment 14. In a further embodiment, the inner cylindrical component 34B in the closed position fluidically seals the interior of the segment 14 from the exterior.

In contrast, FIGS. 2A and 3 depict the segments 12A, 12B, 14 in their open configurations. In these configurations, each of the inner cylindrical components 30B, 32B, 34B are positioned such that the openings 36, 38, 40 are open.

In use, according to one embodiment, the inner cylindrical components 30B, 32B, 34B can thus be actuated to move between their closed and their open positions and thereby convert the device 10 between a closed or non-operational configuration (in which the operational components such as the arms 20, 22 and/or the imaging components 26 and/or the lighting components 28 are inoperably disposed within the segments 12A, 12B, 14) and an open or operational configuration (in which the operational components are accessible through the openings 36, 38, 40 and thus capable of operating). Thus, according to one implementation, the device 10 can be in its closed or non-operational configuration during insertion into a patient's body and/or to a target area and then can be converted into the open or operational configuration by causing the inner cylindrical components 30B, 32B, 34B to rotate into the open configurations.

Alternatively, one or more or all of the segments do not have inner and outer components that rotate in relation to each other.

It is understood that the various embodiments of the device 10 disclosed herein include appropriate actuation components to generate the force necessary to operate the arms and/or the rotatable cylinders in the segments. In one embodiment, the actuation components are motors. For example, segment 12A has a motor (not shown) operably coupled with the arm 20 and configured to power the movements of the arm 20. Similarly, segment 12B also has a motor (not shown) operably coupled with the arm 22 and configured to power the movements of the arm 20. In further embodiments, each of the segments 12A, 12B, 14 also have motors (not shown) operably coupled to one or both of the inner and outer cylinder of each segment to power the rotation of the cylinders in relation to each other. In one embodiment, each segment can have one motor to power all drivable elements (arms, cylinders, etc.) associated with that segment. Alternatively, a separate motor can be provided for each drivable element.

Figure 2B:
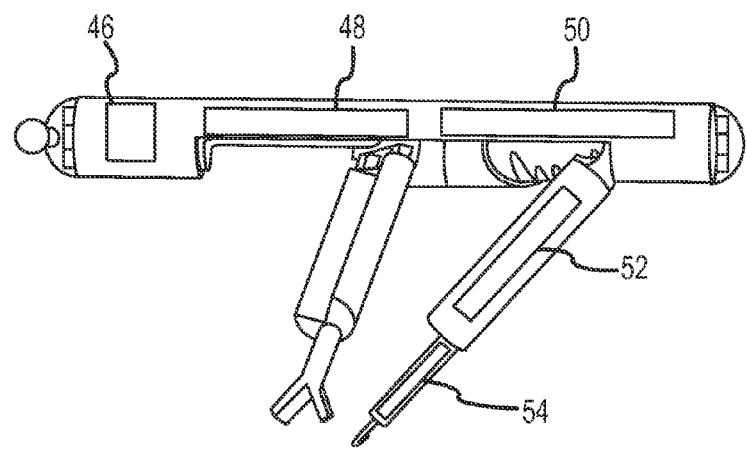
FIG. 2B is a perspective side view of the device of FIG. 1A.
Figure 2C:
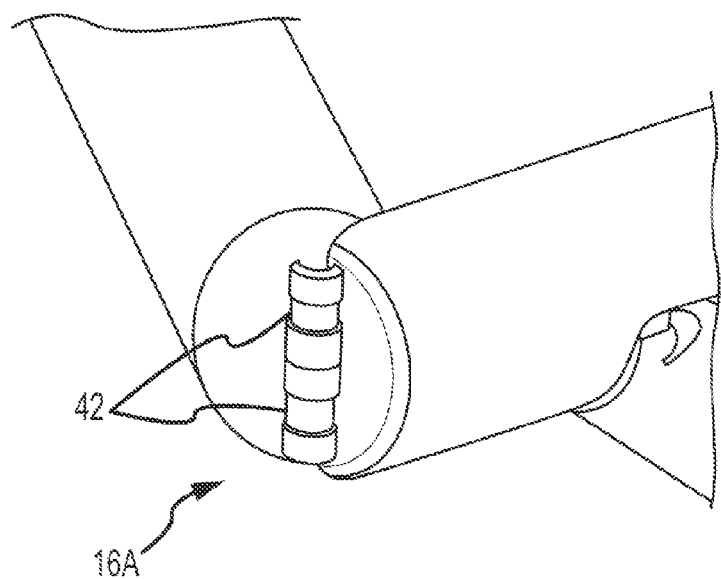
FIG. 2C is a perspective close-up view of a portion of the device of FIG. 1A.

In one embodiment, the joints 16A, 16B are configured to urge the segments 12A, 12B from the insertion configuration of FIG. 1A into the triangular configuration of FIG. 1B. That is, the joints 16A, 16B have torsion springs or some other known mechanism for urging the segments 12A, 12B to rotate around their joints 16A, 16B. For example, FIG. 2C depicts one embodiment in which the joint 16A has torsion springs 42 that are configured to urge segment 12A toward the triangular configuration.

In use, in accordance with one implementation, the device 10 in the insertion configuration as shown in FIG. 1A can be inserted into a patient's body through an incision, a trocar port, or natural orifice in the direction indicated by arrow A. Alternatively, the device 10 can be inserted in the other direction as well. After insertion and/or as the device 10 enters the target area or procedural area in the patient's body, the joints 16A, 16B with the torsion springs (or other standard mechanisms) urge the segments 12A, 12B from their insertion position to their triangular position. As the segments 12A, 12B contact each other to form joint 18, the two segments are coupled together with mating components that semi-lock the segments 12A, 12B together. That is, the two segments 12A, 12B can only be separated at the joint 18 by a force sufficient to overcome the semi-lock. Any such known mating component or coupling component, including any mechanical or magnetic mating component(s), can be incorporated into the device 10 for this purpose.

Thus, according to one embodiment, the device 10 can be in its insertion configuration during insertion into the patient. As the device 10 enters the target cavity and exits the port or incision, the torsion springs or other mechanisms at the joints 16A, 16B cause the two segments 12A, 12B to move toward each other until they couple to form the triangular configuration. The device 10 can then be attached to the abdominal wall by some method such as an external magnetic handle. Alternatively, the device 10 can be positioned anywhere in the cavity of the patient as desired by the user. The device 10 is then used to perform some sort of procedure.

Subsequently, when the procedure is complete, the device 10 can be retracted from the cavity. To do so, the surgeon uses a grasping or retrieval tool such as a Endo Babcock grasper made by Covidien in Mansfield, Mass., to attach to or otherwise grasp the ball 44 at the joint 18 and apply sufficient force to overcome the semi-lock of the joint 18. Alternatively, any retrieval component can be positioned at the end of segment 12A or elsewhere on the device 10 for grasping or otherwise coupling to for purposes of removing the device 10 from the patient's body. When the coupling of the semi-lock is overcome, the force urges the segments 12A, 12B away from each other, thereby making it possible for the surgeon to pull the ball 44 through a port or incision and out of the patient, thereby forcing the device 10 into its insertion configuration.

The multiple segments provided in the various embodiments of the device disclosed herein result in significantly more payload space than a single cylindrical body. The increased payload space results in increased capabilities for the device in the form of more, bigger, or more complex operational components, more, bigger, or more complex motors, magnets (as described below) and other similar benefits relating to the availability of more space for more, bigger, or more complex components. For example, FIG. 2B depicts a side view of the device 10 according to one embodiment that shows the payload space available in segment 12B. More specifically, segment 12B and its coupled arm 22 have payload spaces 46, 48, 50, 52, 54 that can be used to accommodate motors, operational components, sensors, magnets (as described below) or any other type of component that could be useful for a procedural device. Similarly, each segment 12A, 12B, 14 can have such payload spaces. In addition, the segments 12A, 12B, 14 allow for maximization of the payload space available across the segments 12A, 12B, 14 by distributing the components such as motors, operational components, or magnets to maximize their effectiveness while minimizing the amount of space required by each such component. For example, it might maximize effectiveness of the device 10 while minimizing the utilized space to have one large motor in one segment that provides force for operation of components in more than one segment.

It is understood that various embodiments of the segmented devices disclosed herein are in vivo devices that can be inserted into and positioned within a patient's body to perform a procedure. In one embodiment, an external controller is also provided that transmits signals to the device 10 to control the device 10 and receives signals from the device 10. In one embodiment, the controller communicates with the device 10 wirelessly. Alternatively, the controller and the device 10 are coupled via a flexible communication component such as a cord or wire (also referred to as a "tether") that extends between the device 10 and the controller.

Figure 5:
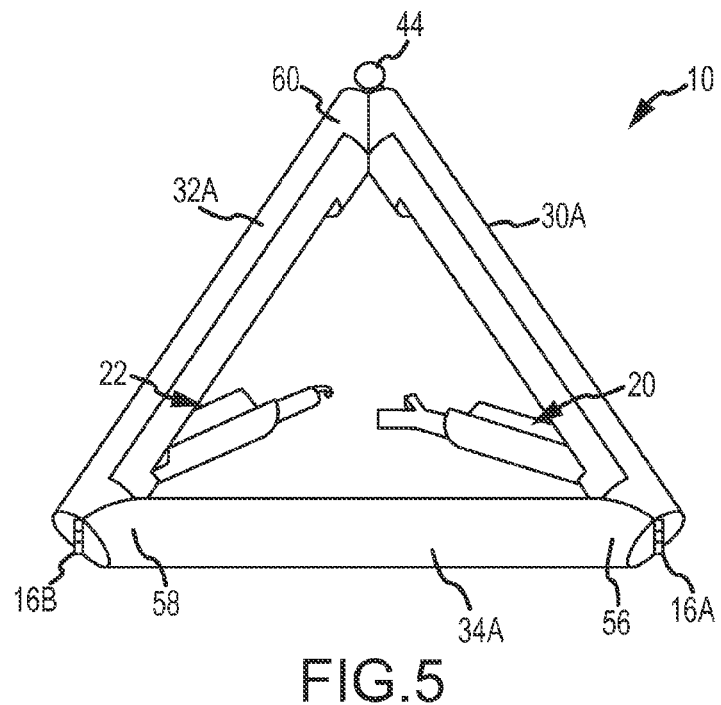
FIG. 5 is a top view of the device of FIG. 1A.

It is also understood that various embodiments of the devices disclosed herein can be used in conjunction with known attachment components to attach or otherwise position the device near, against, or adjacent to an interior cavity wall inside the patient. In one embodiment, the attachment components are one or more magnets, disposed within the device, that communicate magnetically with one or more magnets positioned outside the patient's body. The device magnets can be positioned on or in the device in any suitable configuration. For example, the device magnets in one embodiment can be positioned within the segments 12A, 12B, 14 at positions 56, 58, 60 as shown in FIG. 5. It is understood that the external magnets can be used outside the body to position and/or move the device 10 inside the body.

Figure 6:
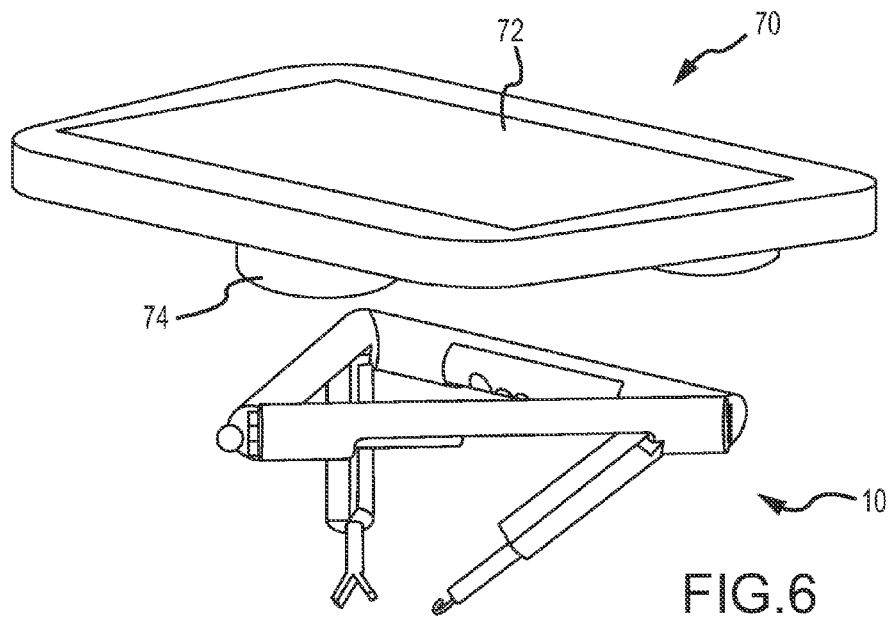
FIG. 6 is a perspective view of modular medical device control and visualization system, according to one embodiment.

It is further understood that various embodiments of the devices disclosed herein can be used in conjunction with known visualization and control components, such as the console 70 depicted in FIG. 6. The console 70 has a display 72 and magnets 74 and is positioned outside the patient such that the magnets 74 can be in magnetic communication with the device magnets (not shown) disposed within or otherwise coupled with the device 10. The console 70 can be used to move the device 10 by moving the console 70 outside the body such that the device 10 is urged to move inside the body, because the console magnets 10 are magnetically coupled with the device magnets (not shown) within the device 10 such that the device 10 remains substantially fixed in relation to the console 70. In addition, it is understood that the triangular (and quandrangular) devices disclosed and described in relation to FIGS. 1A-7 can be used in conjunction with any of the external controller or visualization components and systems disclosed and discussed above and in the applications incorporated above.

The segmented device 10, according to one embodiment, provides greater stability and operability for the device 10 in comparison to other in vivo devices. That is, a device having more than one segment such as device 10 provides for a configuration with a larger "footprint" for the device 10, thereby resulting in greater stability and leverage during use of the device 10. For example, the device 10 with the triangular configuration in FIG. 6 that is urged against the interior cavity wall of the patient by the console magnets 74 has greater stability and leverage in comparison to a device that has a smaller "footprint." That is, the device 10 can have at least three magnets (not shown) disposed at the three corners of the triangular configuration such that when the device 10 is magnetically positioned against the interior cavity wall, the arms of the device 10 can apply greater force to the target tissues while maintaining the position of the device 10 than a corresponding single cylindrical device body.

Figure 7:
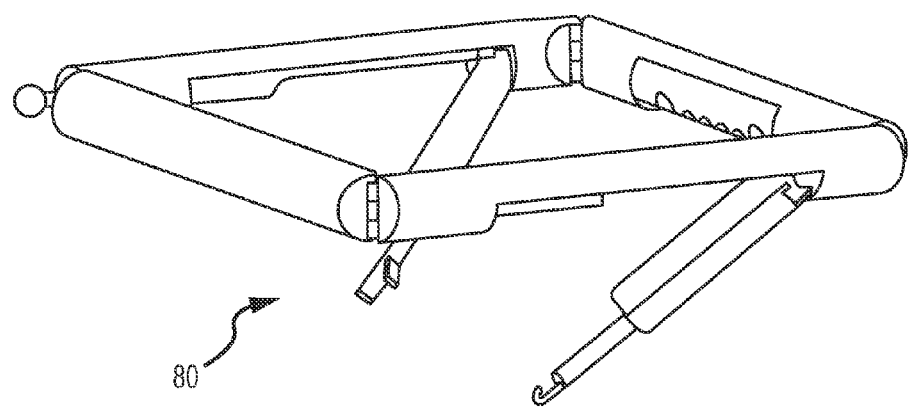
FIG. 7 is a perspective view of a modular medical device, according to one embodiment.

It is understood that the device embodiments disclosed herein are not limited to a triangular configuration. FIG. 7 depicts a device 80 having a quadrangular configuration with four segments. Similarly, devices are contemplated herein having any number of segments ranging from two segments to any number of segments that can be used for a device that can be positioned inside a patient's body. For example, a device incorporating the components and structures disclosed herein could have six or eight segments or more.

Figure 2D:
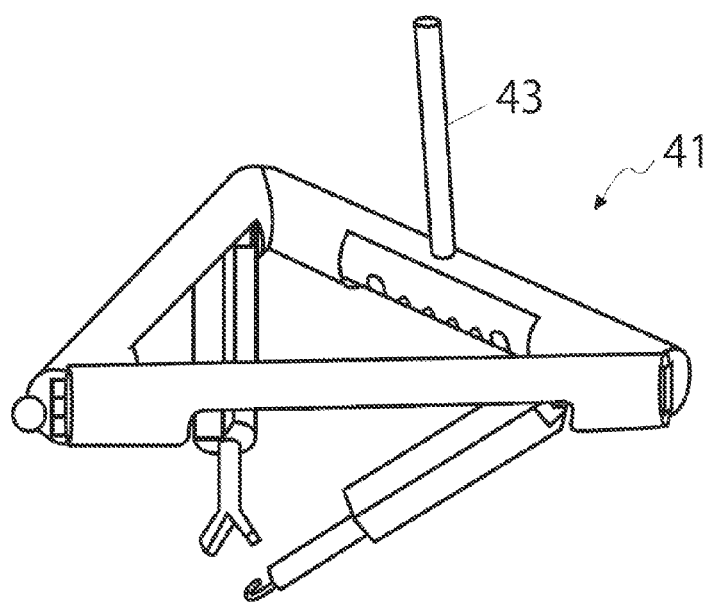
FIG. 2D is a perspective view of another modular medical device, according to a further embodiment.

Several methods of attachment are possible for the triangle robot. A mechanical rod or elongate member having a cross-section of any shape or configuration could be used to support the robot. The elongate member could be rigid or flexible. One example of a rod 43 coupled to a robot 41 is depicted in FIG. 2D, according to one embodiment. The robot could also be placed at the end of other instruments and manual tools as well as at the end of another robot.

In other embodiments, including some discussed above, the attachment mechanism includes magnets. Attaching the robot with magnets can be accomplished in many different ways; some are shown in FIGS. 8A-8C. This can include a magnet external to the patient that is placed against the abdominal wall. This magnet then interacts with the robot to support the robot and hold it in place. The external magnet can interact with a high permeability material on the inside of the patient and attached to the robot as shown in FIG. 8A. The roles could also be reversed and the high permeability material could also be external to the patient and the magnet could be internal.

The external magnet can also interact with a second magnet inside the patient and attached to the robot. This can be done so that opposite poles of the magnet attract using a single pole on each magnet (as shown in FIG. 8B) or by using both poles on each magnet (as shown in FIG. 8C).

The magnet (or high permeability material) associated with the robot does not even need to be attached to the robot. It only needs to interact in such a way as to create a force to stabilize the robot (this stability is described below). For example, when a piece of paper is attached to a refrigerator with a magnet, the magnet is not attached to the paper, but it does create a force that stabilizes the paper on the refrigerator. A similar approach could be used with the robot.

The methods of magnetic attachment described above can be used in many different combinations. For example, any number of magnets (0, 1, 2, 3, . . . ) can be used to attach the robot. One obvious approach would be to place a magnet in each corner (or in each segment) of the triangle of the robot, with a trio of external magnets being used external to the patient. However, the triangle (or other open or closed polygons (from 2 sides on up)) is especially well suited to be supported by several different combinations of magnets. For example, a single magnet can be used inside the triangle since the shape of the triangle will provide multi axis support to react the force applied by this single magnet. This is further described in the next section. A "V" configuration or other polygon could give similar support.

Certain embodiments disclosed herein relate to maximization of stability of the various device embodiments while positioned inside the patient's body. Consider the triangle configuration of the in vivo robot 10 described above in detail and shown in FIG. 9. This is one possible attachment method for the robot. Here a single magnet 90 is attached to the robot 10 so that it is attracted to a magnet 92 on the outside of the patient. The magnet 90 on the robot produces a force on the robot 10 in the upward direction.

Figure 10:
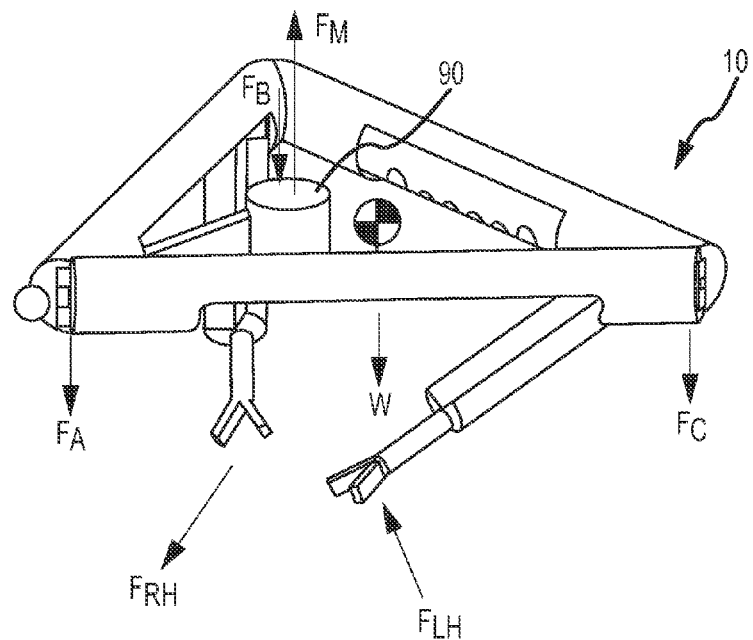
FIG. 10 is a schematic representation of various forces associated with the device of FIG. 1A, according to one embodiment.

A simplified Free Body Diagram (FBD) showing a simplified interpretation of the reaction forces is shown in FIG. 10. Here, the magnet 90 produces an upward force on the body of the robot 10 (assumed rigid) $F_m$. The weight of the robot 10, W, is also shown acting at the center of mass of the robot 10. Each corner of the robot is labeled A, B, and C and reaction forces are shown at each corner ($F_A$, $F_B$, $F_C$). These reaction forces could occur along the length of each side in any distribution depending on the shape of the robot, stiffness of the abdominal wall, and other factors. However, for simplicity, these reaction forces are assumed to be lumped at each corner. Finally, end effector forces ($F_{RH}$, $F_{LH}$) are shown as the robot 10 applies forces to the tissue being manipulated during surgery. Also, any external applied moments or dynamic loads would also need to be included. This analysis could be extended to other robot configurations (e.g. a square robot with three manipulators), as will be described in further detail below.

The stability of the robot 10 in FIG. 10 created by the single magnet 90 can be determined using various mathematical techniques. One example of such techniques is set forth in Papadopoulos, E. and Rey, D., "A New Measure of Tipover Stability Margin for Mobile Manipulators," Proc. of the IEEE International Conference on Robotics and Automation, Minneapolis, Minn., April 1996 (which relates to the stability mathematics of large off-road vehicles). Similar techniques can be used to determine the stability of the robot 10. The simplified version of this analysis is to take sum moments from all external forces (and moments) about each contact line for the robot. A first step in this example would be to sum the moments about the contact line AB (in FIG. 10). If the resulting moment "pushes" the robot into the abdominal wall (such as would be caused by a large magnet force), the configuration is stable and the robot will not fall. If the resulting moment "peels" the robot away from the abdominal wall (such as would be caused by a small magnet force and a large robot weight), the robot would be unstable and would fall away from the abdominal wall. This would then need to be repeated for all contact lines (BC and CA in our example).

The above analysis shows that a single magnet can be used to hold the robot 10 in place.

Figure 11:
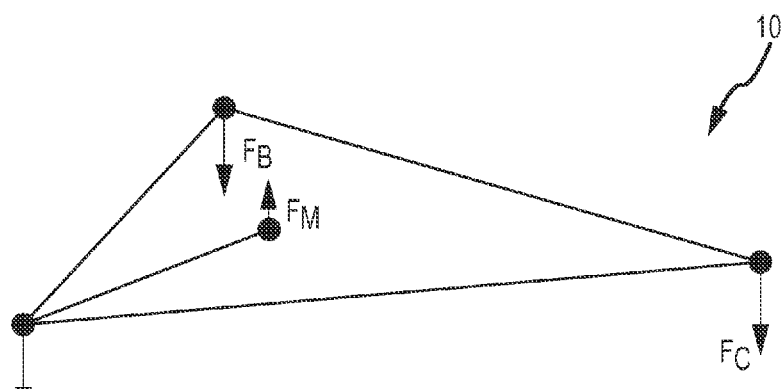
FIG. 11 is a schematic representation of various forces associated with the device of FIG. 1A, according to another embodiment.

A simplified example is shown in FIG. 11. Here, the robot 10 is assumed mass-less and is not applying forces with its end effectors. It can be clearly seen that a large magnetic force, $F_M$, produces moment about the line AB that will cause the robot to rotate into the abdominal wall and therefore make a stable configuration for the robot. The same is true about lines BC and CA.

Figure 12A:
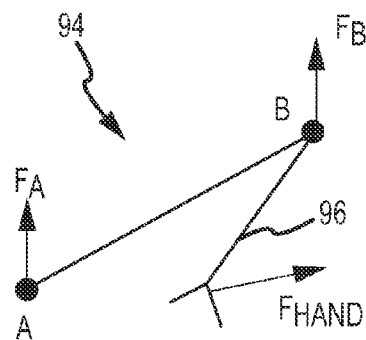
FIG. 12A is a schematic representation of various forces associated with a robotic device.
Figure 12B:
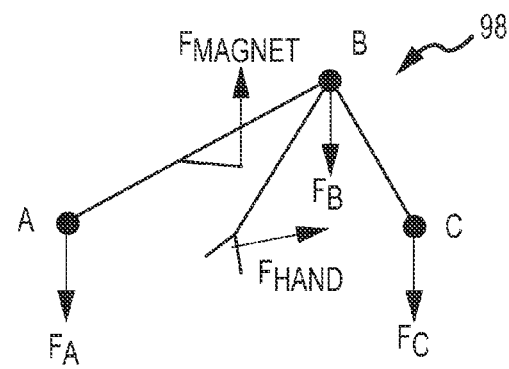
FIG. 12B is a schematic representation of various forces associated with another robotic device, according to one embodiment.

This example in FIG. 11 is further exemplified by the two possible configurations shown in FIGS. 12A and 12B. In this situation, the robot 94 in FIG. 12A could be created by simply using one segment of the triangle configuration as shown back in FIG. 10 (with attachment magnets at A and B). In FIG. 12A, there are two attachment points (A and B) that hold the robot 94 to the upper abdominal wall (one segment). When the robot's end effector (or hand) 96 applies a force in an arbitrary direction, there will be non-zero moments about the contact line AB. This will cause the robot 94 to rotate about the line AB and could result in some instability.

In contrast, FIG. 12 depicts a device 98 that contains additional structure as represented by point C. In this embodiment, hand forces ($F_{Hand}$) that produce a moment about the contact line AB can be balanced by a moment created by the reaction force at point C ($F_C$). Similarly, moments can be balanced and a stable configuration produced when other lines of contact are considered (BC & AC in this case, with other possibilities described below). Again, discrete points (A, B, & C) are described to simplify the description, but any line segment (AB for example) could be a continuous line of contact.

Figure 13:
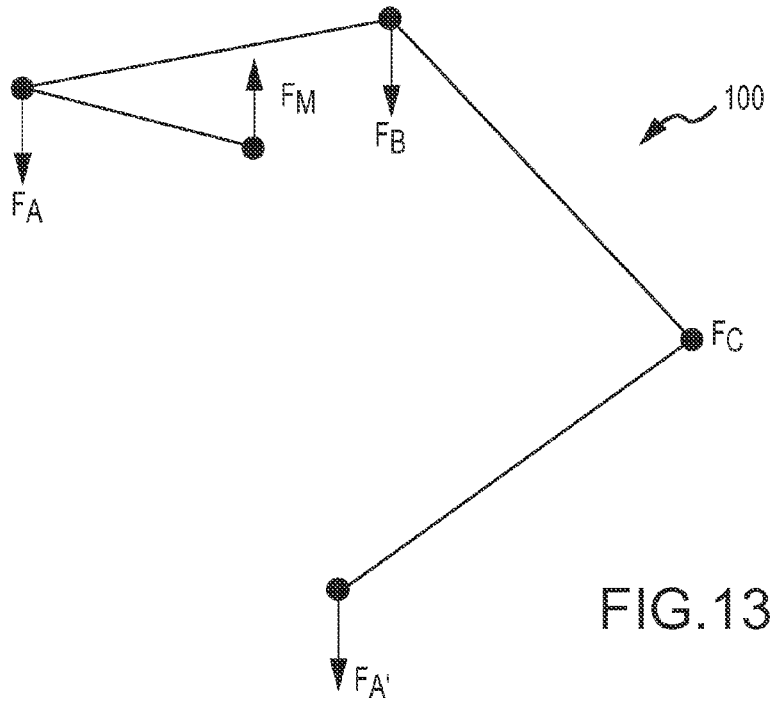
FIG. 13 is a schematic representation of various forces associated with another robotic device, according to another embodiment.

This stability based on one magnet can be recreated in several robot configurations. For example, FIG. 13 shows a configuration similar to FIG. 11, but the "triangle" in FIG. 13 is in an "open" configuration 100 in which point A now becomes two points (A and A'). This configuration 100 will also produce stability if the moments about all contact lines (AB, BC, CA' and A'A) "pushes" the robot into the abdominal wall rather than "peeling" it away.

Figure 14:
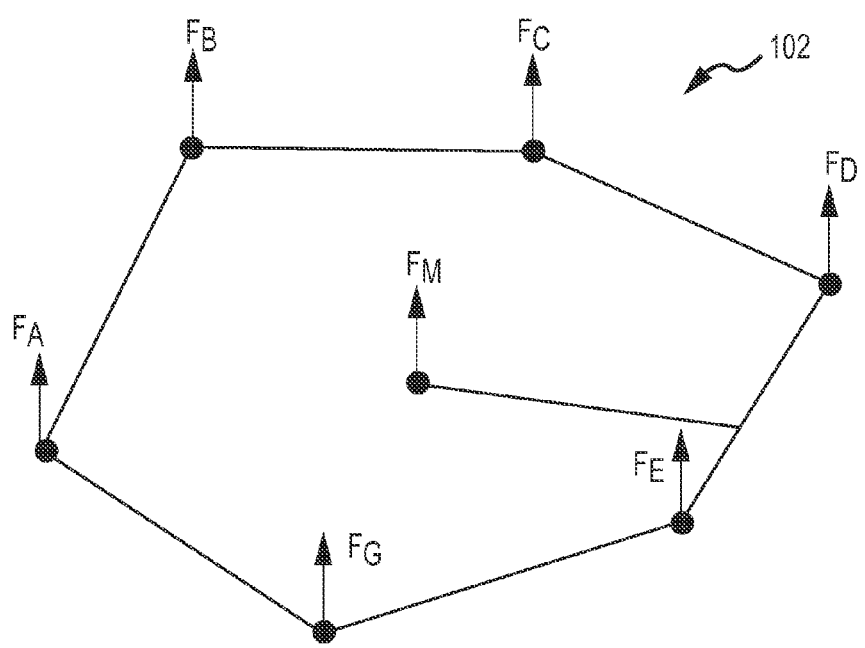
FIG. 14 is a schematic representation of various forces associated with yet another robotic device, according to a further embodiment.

FIG. 14 depicts another example of a multi-sided polygon 102 that uses a single magnet for stable attachment. The same analysis used above applies here and can be used to show that the robot 102 can be stable. In addition, the stability provided by a single magnet as described with the configurations discussed above can also occur for shapes other than polygons. For example, a "V" or "T" configuration could be used. The shapes could be open or closed.

It is understood that the concept of robot reaction forces (e.g. $F_A$, $F_B$, etc) occurring at a single point is an oversimplification for purposes of this discussion. These forces can occur at a continuum across any segment of any portion of the robot (or at discrete points).

In certain embodiments, different combinations of magnet "types" can also be used. For example, the robot could have a magnet at one corner of the robot and two pieces of high permeability material at the other two corners (or sides). Or the robot could have two magnets and one piece of high permeability material, or other combinations.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Although the present invention has been described with reference to preferred embodiments, persons skilled in the art will recognize that changes may be made in form and detail without departing from the spirit and scope of the invention.

What is claimed is:

1. A segmented medical device, the system comprising:
   (a) a first body segment configured to be disposed inside a cavity of a patient, the segment comprising
      (i) a first operational component associated with the first body segment; and
      (ii) a first mating component at a first end of the first body segment;
   (b) a second body segment configured to be disposed inside the cavity of the patient, the segment comprising
      (i) a second operational component associated with the second body segment; and
      (ii) a first pivotal coupling at a first end of the second body segment, whereby the second body segment is pivotally coupled to a second end of the first body segment;
   (c) a third body segment configured to be disposed inside the cavity of the patient, the segment comprising
      (i) a third operational component associated with the third body segment;
      (ii) a second pivotal coupling at a first end of the third body segment, whereby the third body segment is pivotally coupled to a second end of the second body segment; and
      (iii) a second mating component at a second end of the third body segment, the second mating component configured to be coupleable with the first mating component; and
   (d) an attachment component associated with the segmented medical device, wherein the attachment component comprises a rod coupled to the segmented medical device, wherein the rod is configured to extend from the segmented medical device out of the cavity of the patient.

2. The segmented medical device of claim 1, wherein the device is configured to move between an open position in which the first and second mating components are not coupled together and a closed position in which the first and second mating components are coupled.

3. The segmented medical device of claim 2, wherein the first, second, and third body segments define an opening in the closed position.

4. The segmented medical device of claim 3, wherein the attachment component is disposed in the opening.

5. The segmented medical device of claim 1, wherein the first pivotal coupling and the second pivotal coupling comprise tensioned components configured to urge the first mating component and the second mating component toward each other.

6. The segmented medical device of claim 1, wherein the first body segment comprises a first inner cylindrical component disposed within a first outer cylindrical component, wherein the first inner cylindrical component is rotatable in relation to the first outer cylindrical component.

7. The segmented medical device of claim 6, wherein the first inner cylindrical component comprises a first inner opening and the first outer cylindrical component comprises a first outer opening, wherein the first inner cylindrical component and the first outer cylindrical component are rotatable such that the first inner opening and first outer opening align, thereby providing access to an interior portion of the first inner cylindrical component.

8. The segmented medical device of claim 7, wherein the first operational component is configured to move between an undeployed position disposed within the interior portion of the first inner cylindrical component and a deployed position in which a portion of the first operational component is disposed outside of the first inner cylindrical component through the first inner opening and first outer opening.

9. A segmented medical device, the system comprising:
   (a) a first body segment configured to be disposed inside a cavity of a patient, the segment comprising
      (i) a first operational component associated with the first body segment; and
      (ii) a first mating component at a first end of the first body segment;
   (b) a second body segment configured to be disposed inside the cavity of the patient, the segment comprising
      (i) a second operational component associated with the second body segment; and
      (ii) a first pivotal coupling at a first end of the second body segment, whereby the second body segment is pivotally coupled to a second end of the first body segment;
   (c) a third body segment configured to be disposed inside the cavity of the patient, the segment comprising
      (i) a third operational component associated with the third body segment;
      (ii) a second pivotal coupling at a first end of the third body segment, whereby the third body segment is pivotally coupled to a second end of the second body segment; and
      (iii) a second mating component at a second end of the third body segment, the second mating component configured to be coupleable with the first mating component; and
   (d) an attachment component disposed in a substantially central location when the segmented medical device is in a closed configuration in which the first and second mating components are coupled, wherein the segmented medical device is configured to move between the closed configuration and an open configuration in which the first and second mating components are not coupled together.

10. The segmented medical device of claim 2, wherein the first, second, and third body segments define an opening in the closed position, wherein the attachment component is disposed in the substantially central location in the opening.

11. The segmented medical device of claim 9, wherein the attachment component comprises a single magnet disposed in a substantially central location when the segmented medical device is in a closed configuration.

12. The segmented medical device of claim 1, wherein
 (a) the first body segment comprises a first inner cylindrical component disposed within a first outer cylindrical component, wherein the first inner cylindrical component is rotatable in relation to the first outer cylindrical component;
 (b) the second body segment comprises a second inner cylindrical component disposed within a second outer cylindrical component, wherein the second inner cylindrical component is rotatable in relation to the second outer cylindrical component; and
 (c) the third body segment comprises a third inner cylindrical component disposed within a third outer cylindrical component, wherein the third inner cylindrical component is rotatable in relation to the third outer cylindrical component.

13. The segmented medical device of claim 12, wherein
 (a) the first inner cylindrical component comprises a first inner opening and the first outer cylindrical component comprises a first outer opening, wherein the first inner cylindrical component and the first outer cylindrical component are rotatable such that the first inner opening and first outer opening align, thereby providing access to an interior portion of the first inner cylindrical component;
 (b) the second outer cylindrical component comprises a second outer opening, wherein the second inner cylindrical component and the second outer cylindrical component are rotatable such that the second operational component is accessible through the second outer opening; and
 (c) the third inner cylindrical component comprises a third inner opening and the third outer cylindrical component comprises a third outer opening, wherein the third inner cylindrical component and the third outer cylindrical component are rotatable such that the third inner opening and third outer opening align, thereby providing access to an interior portion of the third inner cylindrical component.

14. The segmented medical device of claim 13, wherein (a) the first operational component is configured to move between an undeployed position disposed within the interior portion of the first inner cylindrical component and a deployed position in which a portion of the first operational component is disposed outside of the first inner cylindrical component through the first inner opening and first outer opening; and (b) the third operational component is configured to move between an undeployed position disposed within the interior portion of the third inner cylindrical component and a deployed position in which a portion of the third operational component is disposed outside of the third inner cylindrical component through the third inner opening and third outer opening.

15. The segmented device of claim 14, wherein the first operational component comprises a grasper and the second operational component comprises a cautery hook.

16. The segmented device of claim 1, wherein the second operational component comprises at least one camera or at least one light.

* * * * *